United States Patent [19]

Cheever

[11] 4,305,000
[45] Dec. 8, 1981

[54] PROCESS OF AND APPARATUS FOR COLD-CATHODE ELECTRON-BEAM GENERATION FOR STERILIZATION OF SURFACES AND SIMILAR APPLICATIONS

[75] Inventor: Richard N. Cheever, Acton, Mass.

[73] Assignee: Tetra Pak Developpement Ltd., Lausanne, Switzerland

[21] Appl. No.: 957,483

[22] Filed: Nov. 3, 1978

[51] Int. Cl.³ .............................................. H01J 37/00
[52] U.S. Cl. ............................. 250/492.3; 250/492.1
[58] Field of Search .......... 250/492 R, 492 B, 396 R, 250/398; 313/326; 315/56, 58, 250

[56] References Cited

U.S. PATENT DOCUMENTS

| | | | |
|---|---|---|---|
| 2,429,217 | 10/1947 | Brasch | 250/492 B |
| 2,924,714 | 2/1960 | Davis et al. | 250/492 P |
| 3,144,552 | 8/1964 | Schonberg et al. | 250/492 B |
| 3,406,304 | 10/1968 | Brewster | 250/492 B |
| 3,780,308 | 12/1973 | Nablo | 250/492 B |

*Primary Examiner*—Bruce C. Anderson
*Attorney, Agent, or Firm*—Rines and Rines, Shapiro and Shapiro

[57] ABSTRACT

This disclosure is concerned with a process of and apparatus for producing relatively low energy electron beams through pulsed cold-cathode beam generation in a mode of operation involving an important intermediate region of a substantially linear depth-dose profile characteristic that reduces the sensitivity to possible voltage variations, and with improved triggering structures that significantly improve reliability and minimize erratic pulse generation and missing pulses, thus particularly adapting the process and apparatus for such stringent applications as production-line sterilization of surfaces, materials or workpieces passed by the apparatus.

24 Claims, 6 Drawing Figures

PROCESS OF AND APPARATUS FOR COLD-CATHODE ELECTRON-BEAM GENERATION FOR STERILIZATION OF SURFACES AND SIMILAR APPLICATIONS

The present invention relates to processes of and apparatus for electron-beam generation for sterilization and other irradiation of surfaces, materials and workpieces of various types, being more particularly concerned with the cold-cathode pulsed electron-beam generation of relatively low energy electrons (say, of the order of 50–450 keV) with a high degree of reliability.

BACKGROUND OF INVENTION

Relatively low energy electron beams have been used successfully for such applications as surface sterilization and the surface treatment of containers and other articles, materials or workpieces, as described, for example, in U.S. Pat. No. 3,780,308, of Energy Sciences Inc., the assignee of the present application. Bulk electron-sterilization techniques are disclosed in U.S. Pat. No. 3,779,796, of said Energy Sciences Inc. In such applications as packaging material sterilization, direct-current beam generators of the type marketed under the trademark "Electrocurtain," by said Energy Sciences Inc., have been employed; such low energy electron beam generation being described, for example, in U.S. Pat. Nos. 3,702,412; 3,745,396; and 3,769,600.

There are advantages, in some applications, as mentioned in said Letters Patent, in the use of repetitive-pulse-production of such relatively low energy electron beams with the aid of cold-cathode electron sources, and with capacitor-discharge pulsing techniques of the type previously used in other types of pulse generators, including the Marx-type capacitor storage-spark-discharge generators long-applied to high-energy physics systems, among the more recent of which is the pulsing of lasers, as described in *Physics Today*, April, 1975. (Also, E. Ault et al., IEEE J. Quant. Elec., Vol. 10, p. 624, on [1974]).

Among the considerations in applying such techniques to the problems of the present invention, however, are the very serious consequences of even temporary erratic pulsing or the missing of pulses, which, when occuring in a production-line sterilization application, for example, can result in the potentially dangerous effect of failing to sterilize at all, or improperly or inadequately sterilizing the workpiece as a result of poor beam uniformity, directivity and the like. A new level of reliability over prior uses of these pulse techniques in other applications is thus required for the purposes of the present invention. Further, prior systems using such techniques were often directed to laboratory and experimental applications which did not require the longevity of operation and industrial reliability underlying the commercial requirements of production-line sterilization and the like.

It has been determined that one of the keys to the unreliability (for present purposes) of previous pulse techniques of this character has been the absence of a sufficiently wide triggering range of the spark-discharge gaps. Previously, fixed gap trigger generators have operated at relatively narrow triggering ranges of approximately 15 percent below the self-breakdown voltage; or, where dynamic range variation has been required, with manual adjustments of gap spacing or by multiple triggered gaps, clearly unsuitable for production-line operation. Near the upper end of the triggering range, occasional prefires will cause low output voltages; while near the lower end of the triggering range, occasional misses occur. In accordance with the present invention, on the other hand, triggering range capacity has been extended upwards of about 30 percent—operation found necessary for long service industrial life time.

Among the novel pulsing circuit features of the invention, are significantly improved and tailored conductive shield structures for increasing the stray capacitance to ground along the capacitor stack, and large-area spark gaps of the "rail" type with novel trigger location and operation. Underlying the invention, moreover, is the discovery of a technique for obtaining a novel substantially linear depth-dose profile characteristic, and an intermediate region of operation thereupon, that startlingly renders the effects of the electron beam impulses significantly less sensitive to possible voltage variations during the pulse generation, thus promoting substantially uniform irradiation of surfaces and workpieces (sometimes herein generically termed "products") passing the apparatus.

Accordingly, an object of the present invention is to provide a new and improved process of and apparatus for the generation of relatively low voltage, energetic electron beam pulses which are not subject to the above-described limitations and disadvantages, but that possess the increased reliability needed for many industrial applications, such as sterilization, and that, in large measure is attained by a significantly increased triggering range and by operation in a most-favored region of a relatively low-slope depth-dose profile characteristic of the generated beam.

Another object of the invention is to provide a new and improved pulse-generating capacitor bank construction that allows for a greatly increased range of voltage variation within which operation of the system is permissible, and with a concomitant increase in reliability.

Other and further obects will be described hereinafter and are more particularly delineated in the appended claims.

In summary, however, the invention contemplates a process of and apparatus for the irradiation of objects by energetic electron particles wherein the reliability of pulse generation has been so greatly enhanced as to make such techniques available to a broader range of commercial applications. In one of its important aspects, the invention embodies a method of insuring the reliability of the production of repetitive impulses of electron-beam energy for production-line sterilization and similar purposes, that comprises, repetitively generating electric-discharge pulses; applying the pulses repetitively to draw electron beam impulses from a cold cathode to and through an electron-pervious window means; disposing the window anode adjacent a portion of a region along which products-to-be-electron-beam-irradiated are passed; adjusting the impedance presented by the cold cathode-window anode to the impendence presented by the pulse generating step to produce a substantially linear electron-beam dose versus penetration depth characteristic curve of relatively low slope in the region near the one-half dose region of said characteristic curve, thereby to reduce the sensitivity of the electron beam impulses to possible voltage variations during the pulse generating step in order to insure substantially uniform irradiation of the products passing along said region. Preferred details are hereinafter presented.

The invention will now be described with reference to the accompanying drawings, FIG. 1 of which is a graph contrasting a dose-depth profile characteristic attained in accordance with the invention with prior characteristics;

Before discussing the preferred apparatus and techniques of operation it is in order to explain the before-mentioned discovery of the rather critical mode of operation of the cold-cathode-generated beam and its tailoring to a preferred substantially linear depth-dose profile characteristic with a highly advantageous intermediate region of operation therealong that reduces sensitivity to possible voltage variation during pulse generation and insures substantially uniform irradiation.

Figure 1:
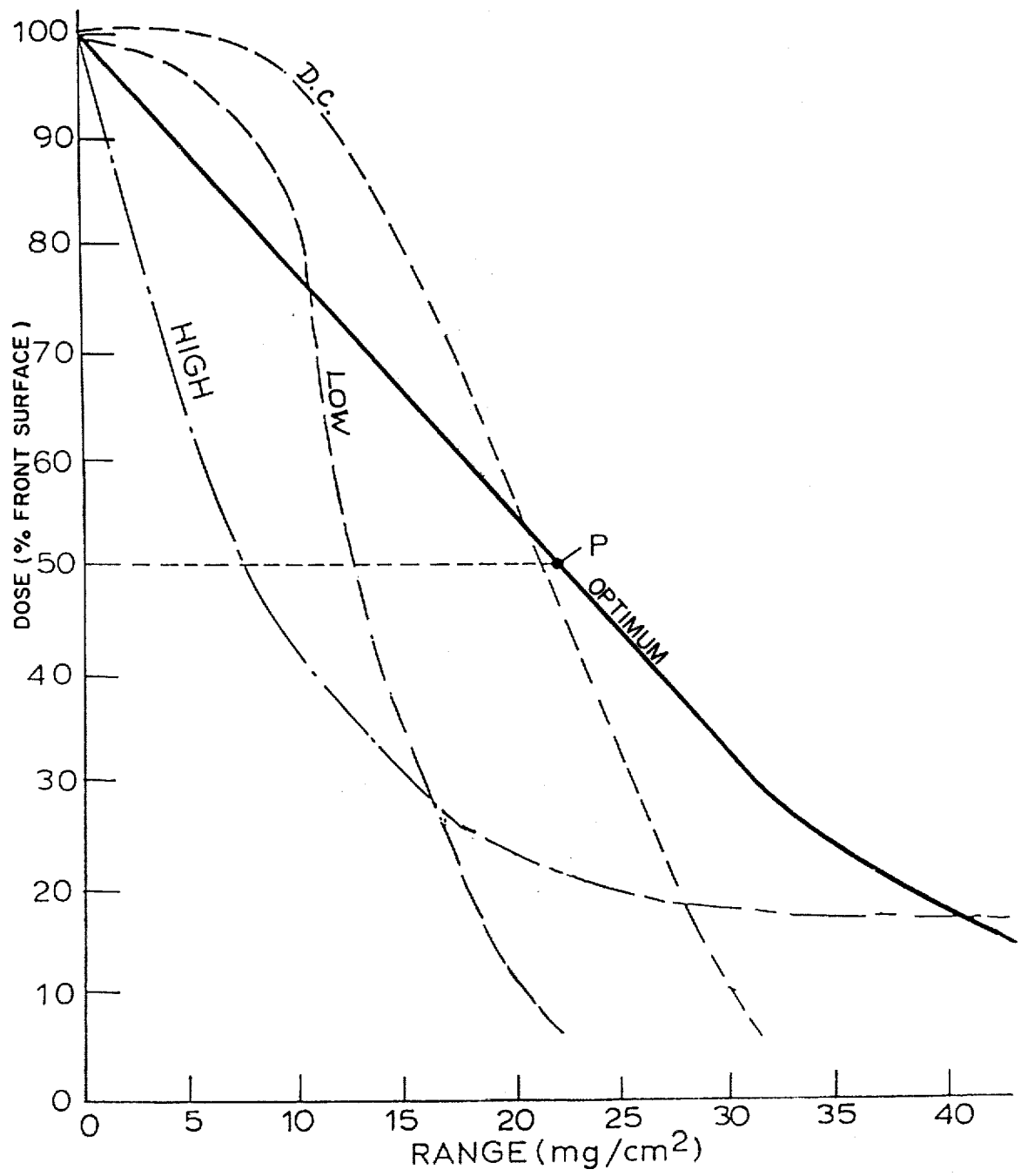

Referring to the graph of FIG. 1, (delivered dose, as a percentage of front product surface, plotted long the ordinate, and range of penetration or depth into the product or other surface wall plotted along the abscissa in mg/cm$^2$), the remarkably linear, relatively low- or moderate-slope curve labelled "OPTIMUM" (having significant curvature only at its lower or right-hand end) represents the type of dose-depth profile characteristic attainable with the novel cold-cathode operation of the invention, as distinguished from those attainable with prior art techniques discussed, for example, in said U.S. Pat. No. 3,780,308 (see more particularly FIG. 1 thereof). With adjustments below and above such optimum conditions, as represented by the steep, non-linear dash-line curve "LOW" and the steep, non-linear dash-dot curve "HIGH" this characteristic is not attained. It is also not attained by machines such as the before-mentioned "Electrocurtain" type D.C. generators, operating with the rather steep, non-linear curve "D.C." of FIG. 1. By operating with as low a slope as possible at the intermediate (near or approximately one-half) dose point P, (say of the order of 45° slope, more or less, as distinguished from the steep angle slopes, including almost 90° slopes, of prior type characteristics of FIG. 1) it has been discovered that such an optimum linear depth-dose profile will enable the generation of substantially constant electron beam impulses with substantially reduced sensitivity to a wide range of possible voltage variations during the pulse generation, thus remarkably insuring substantially uniform irradiation of the products passing by the apparatus.

Such reduced sensitivity, as before stated, does not exist for the steep slope, non-linear profiles of the prior art as indicated at "LOW, " "HIGH" and "D.C." in FIG. 1, the slope of the curve being, indeed, a measure of the sensitivity to voltage changes. Through the obviating of such steep (and non-linear) profiles, the present invention enables reduced sensitivity to voltage variation as before stated. Operation up to and near the intermediate one-half dose point P enables the required depth of sterilization penetration (say, of the order of 20-25 mg/cm$^2$, FIG. 1, or 8-10 mils of penetration in paper wall and the like). That is, the surfaces of the irradiation-penetrated product most remote from the electron beam window are treated near the one-half dose.

The use of pulsed cold-cathode operation, where appropriate, as distinguished from thermionic cathode operation, moreover, results in simplified electronics, lower insulation requirements, decrease in size due to pulse stress considerations, decrease in vacuum requirements for reliable operation, and a substantial decrease in cost of the apparatus. Through the additional use of multiple pulse overlap to avoid the deletereous effects of even statistical spark-gap prefire or miss, such apparatus can provide a new order of reliability and uniform performance that enables the production-line results of the invention.

Figure 2:
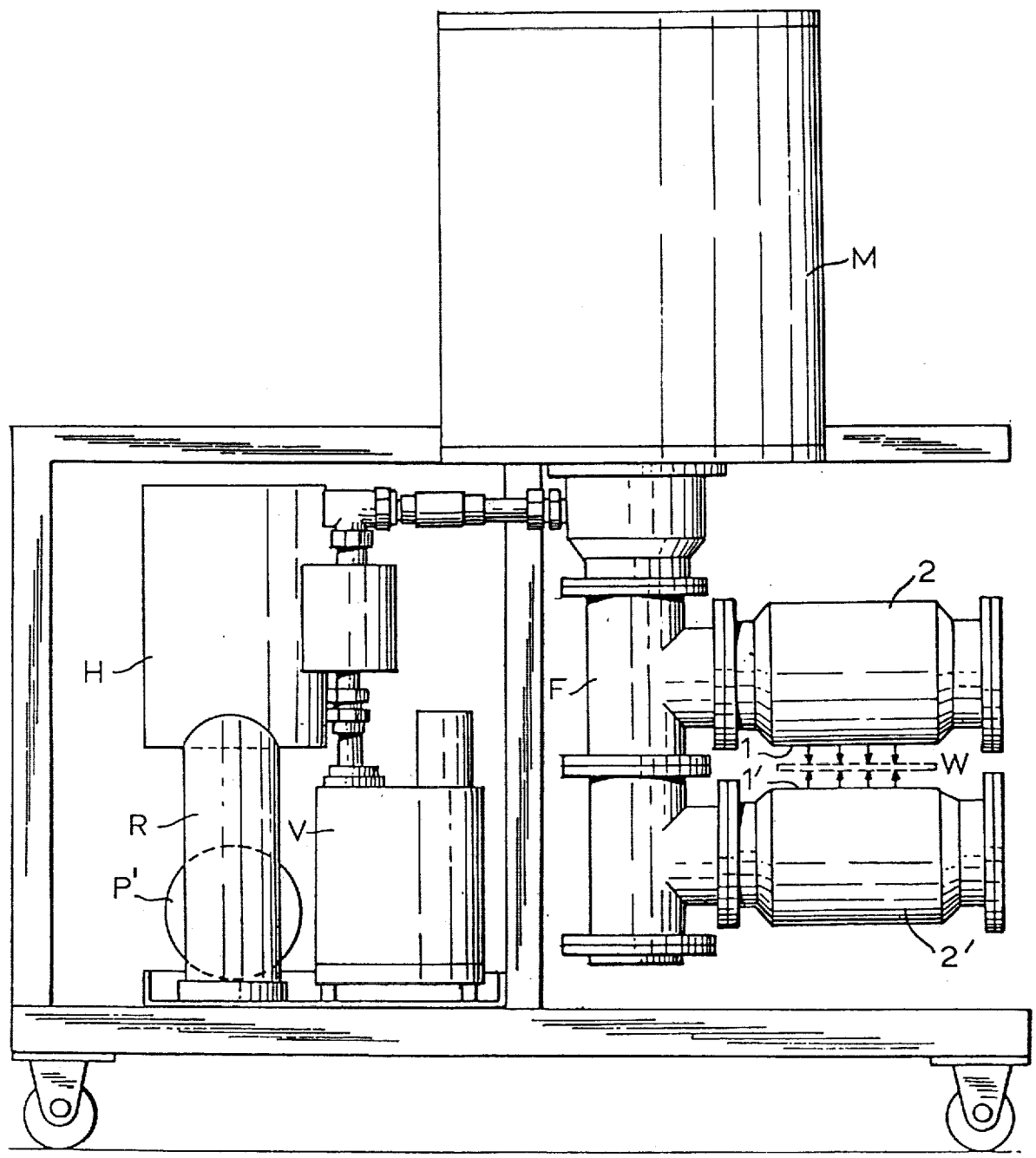
FIG. 2 is a side elevation of an apparatus construction in accordance with a preferred embodiment, using the process underlying the invention.

Referring to the generalized system of FIG. 2, a pair of linear cold-cathode electron beam generators 2 and 2' is shown mounted in general opposition, with their respective electron-permeable windows 1 and 1' irradiating a web W and/or articles carried thereby, as schematically indicated by the arrays of arrows emanating from 1 and 1', with the web W passing continuously into the plane of the drawing (through conventional nitrogen or other gas-contained chamber or zone, as discussed, for example, in said Letters Patent). An array of stacked capacitor-spark-gap Marx-type generator elements, later described, is disposed within an upper pressurized vessel M for driving the cold-cathode generators. A vacuum pump V is provided for the evacuated generator chambers 2 and 2', with the pulse feed conductor section F applying the periodic pulses to the cold-cathode diode structures, later more fully described, and with a cooling system comprising a heat exchanger H, pump P' and liquid reservoir R.

Figure 3:
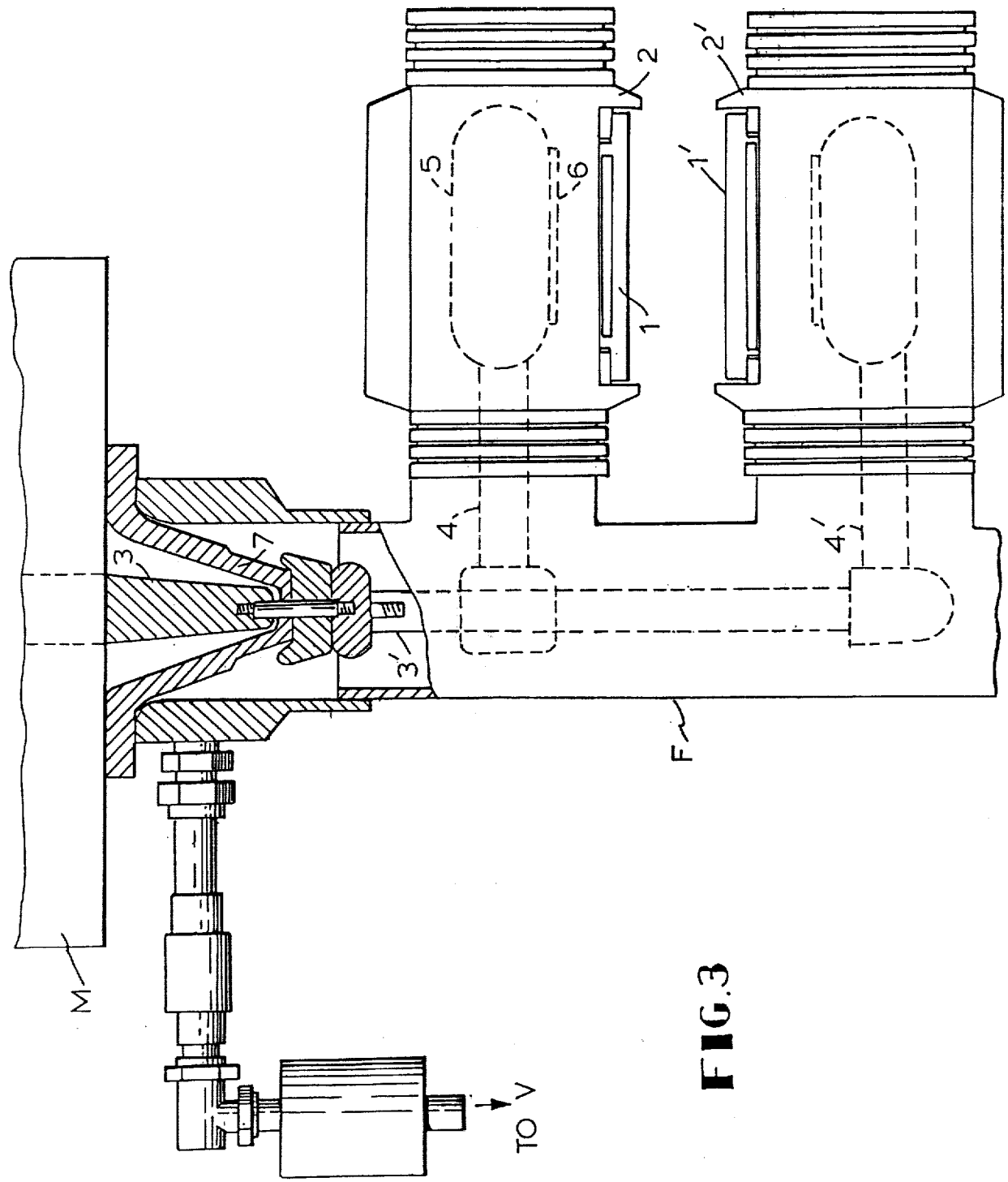
FIG. 3 is a view of the lower right-hand portion of FIG. 2, upon an enlarged scale, and partly sectionalized longitudinally, to illustrate details of the cold-cathode electron beam generators.

Turning, now, to the details of the irradiating generators 2 and 2', this section of the apparatus is shown, in FIG. 3, on a larger scale than in FIG. 2, and in longitudinal section. The driving pulses from the Marx generator in the upper pressurized vessel M are provided between an inner conductor 3 and the outer grounded vessel wall, and are fed via a vertical conductor extension 3' within the evacuated chambers F to a pair of horizontal conductor supports 4 and 4' supporting the respective cold-cathode mounting structures, of which the mount 5 is shown within the chamber 2 (it being understood that a similar structure is provided within chamber 2'). The mount 5 supports the longitudinally extending field-initiated cold cathode gun 6 (as, for example, of longitudinal parallel foil strips, such as of copper, graphite, or copper-graphite composite), facing the longitudinal electron-pervious window 1; it being understood that the cathode of the gun within the chamber 2' will be upwardly pointing toward the window 1'. The grounded outer conductor-wall windows of the chambers 2 and 2' constitute the anodes of the cold-cathode diode guns thus provided. Useful field-initiated cold cathode gun configurations are described, for example, by Loda and DeHart (HQ Defense Nuclear Agency), "Investigation of pulsed cold cathode electron guns for use as a laser discharge sustainer," Physics International Company, DNA 2777F, May, 1972, PIFR-326.

The conical insulating bushing 7 supporting the conductors 3–3' on opposite sides of the apex seals the gas-pressurized chamber M of the spark-gap driving circuits from the vacuum section F-2-2' of the electron beam generators, providing a most convenient high-voltage bushing, as well.

In accordance with the present invention, while the windows 1 and 1' of the electron generators 2 and 2', generally oppose one another, they are rotated slightly relative to one another so that the exiting beams are offset or staggered, though overlapping partially (say, of the order of one beam width) to avoid direct bombardment into one another or other beam interference, and, in sterilizing application, to eliminate the possibility of transfer of organisms from one side of the web passed therebetween to the other.

It has been found, moreover, that there is a most important and determinative relationship or connection between the impedance match effected between the cold-cathode gun and the driver circuits, and the nature both of the depth-dose profile characteristic attained from the resulting electron beams and the pulse spectrum thereof. If the cold-cathode diode gun impedance is too low, the electron spectrum has been found to be dominated by low-energy electrons and the depth-dose profile deviates from the described "OPTIMUM" profile, as shown at "LOW" in FIG. 1; whereas, if the gun impedance is too high, an excess of both low- and high-energy electrons results, with the depth-dose profile curve showing a low half-dose point (as shown at "HIGH" in FIG. 1), but great penetrating power and energy waste thereafter. Through appropriate spacing of the plasma cathode 6 and anode walls, as well as the number and dimensions of the cathode foil strips, the match can be adjusted to attain the desired "OPTIMUM" profile characteristic, and adjustment of pulse repetition rate can achieve operation which produces the novel results previously described.

Figure 4:
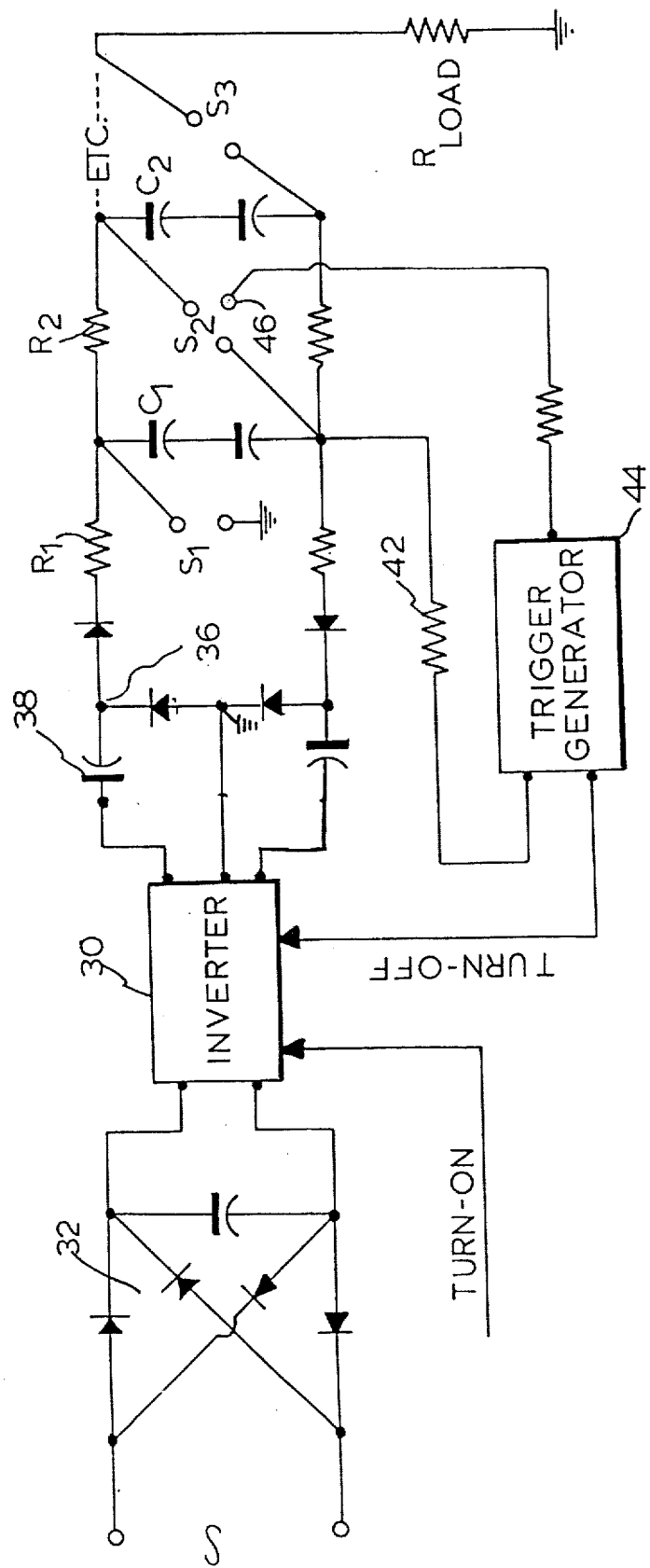
FIG. 4 is a schematic circuit diagram of a preferred Marx-type pulse generator for driving the beam generators of FIG. 3.

It now remains to describe the preferred details of the capacitor-spark gap driver circuit, a simplified schematic diagram of which is illustrated in FIG. 4. Capacitor banks $C_1$-$C_2$-etc. with associated spark gaps $S_1$-$S_2$-$S_3$, etc. forming a Marx-type generator, are charged from a high frequency inverter 30 working directly from line current rectified by a rectifier network 32, as opposed to conventional D.C. charging schemes where more than half of the input power is absorbed in the charging resistors. The high-frequency inverter 30, with a high transformer A.C. voltage output (say, 15 Kv at 10–20 KHz), drives a pair of conventional doubling circuits 36 of opposite polarity, with both polarities charged simultaneously through comparatively small series capacitors 38 (say of the order of 100 picofarads) that pump up the much larger capacitors $C_1$, $C_2$ etc. through isolating resistors $R_1$. Stray capacitance and leakage reactance of the inverter output transformer are used to effect self-resonating in the inverter. The capacitor bank is arranged to charge both positively and negatively simultaneously balanced to ground. Such balanced charging reduces D.C. insulation requirements by one-half. The output (transformer) of the inverter 30 is thus exposed to only the load of the small pump capacitors 38 and pumps charge through the same in both directions. However, each pump capacitor 38 connects to the bank capacitors $C_1$, etc. through a diode, so that the bank is charged in only one direction. The inverter can therefore operate into the bank at zero voltage, because the current out of the inverter is limited by the reactance of the small capacitance.

A sensing resistor 42 measures the voltage on the capacitor bank and feeds back a signal to the trigger generator 44 for comparison with a preset reference. When the charge-sensing signal reaches the preset level, the trigger generator 44 produces an output pulse, commonly in the range of 50 kv, applied to a trigger pin 46 which, in accordance with the invention, is situated in the first full gap or second stage $S_2$ of the pulse generator system. By triggering other than in the first stage $S_1$, which is conventional in such generators as described in the previously cited references, it has been found that a substantial increase in the effective triggering range of the system is obtained, the advantages of which have been previously mentioned. The first gap $S_1$, because it is greatly over-volted, breaks down after gap $S_2$ and then the Marx system fires down the line, over-volting $S_3$ through $C_2$, etc. until the final driving pulse is delivered to the load $R_{LOAD}$, schematically representing the cold-cathode electron gun diodes.

Figure 5:
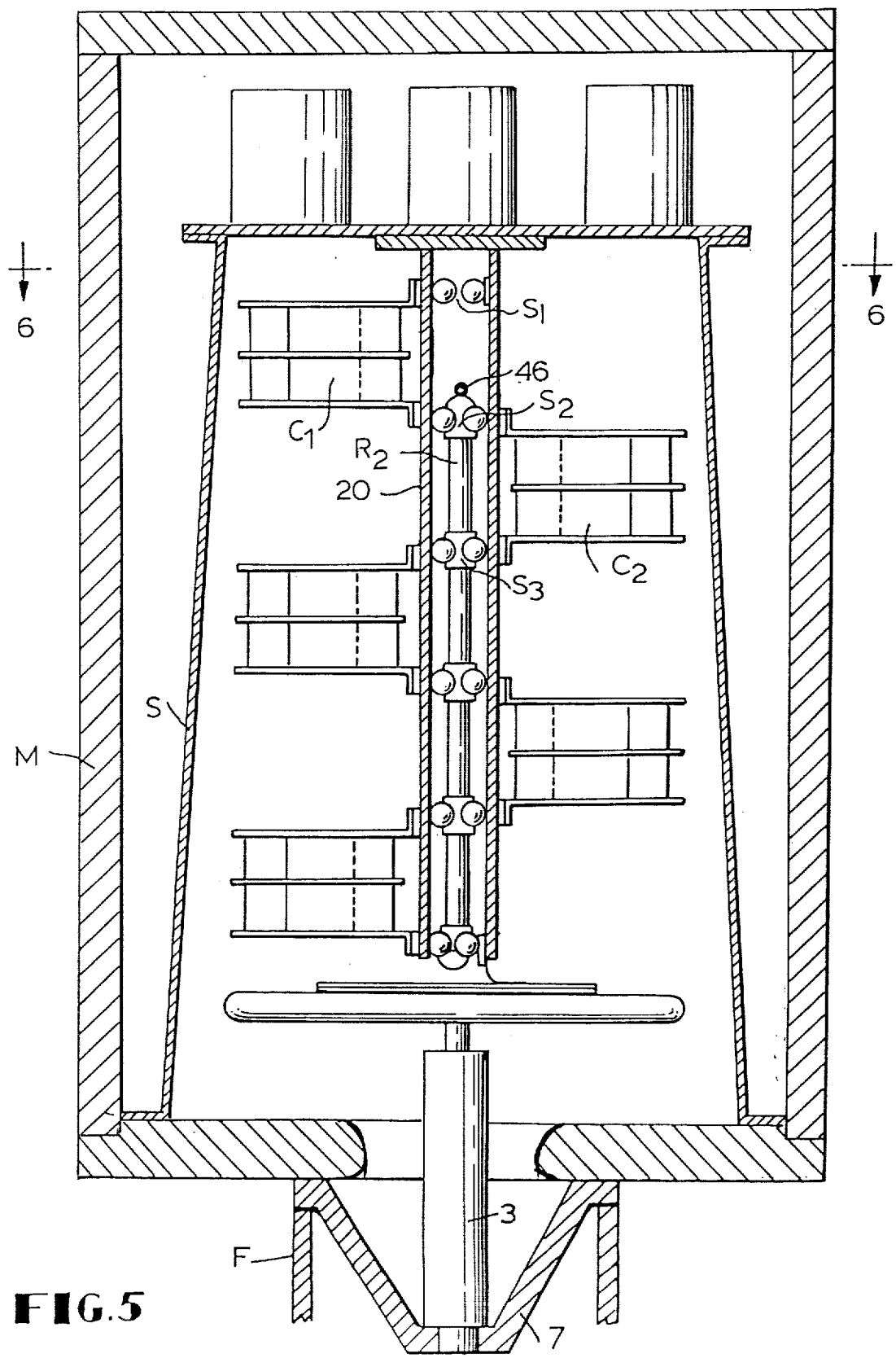
FIG. 5 is a longitudinal section, upon a larger scale, of the upper capacitor-spark gap Marx pulse generator of FIG. 2 and of the circuit type shown in FIG. 4.
Figure 6:
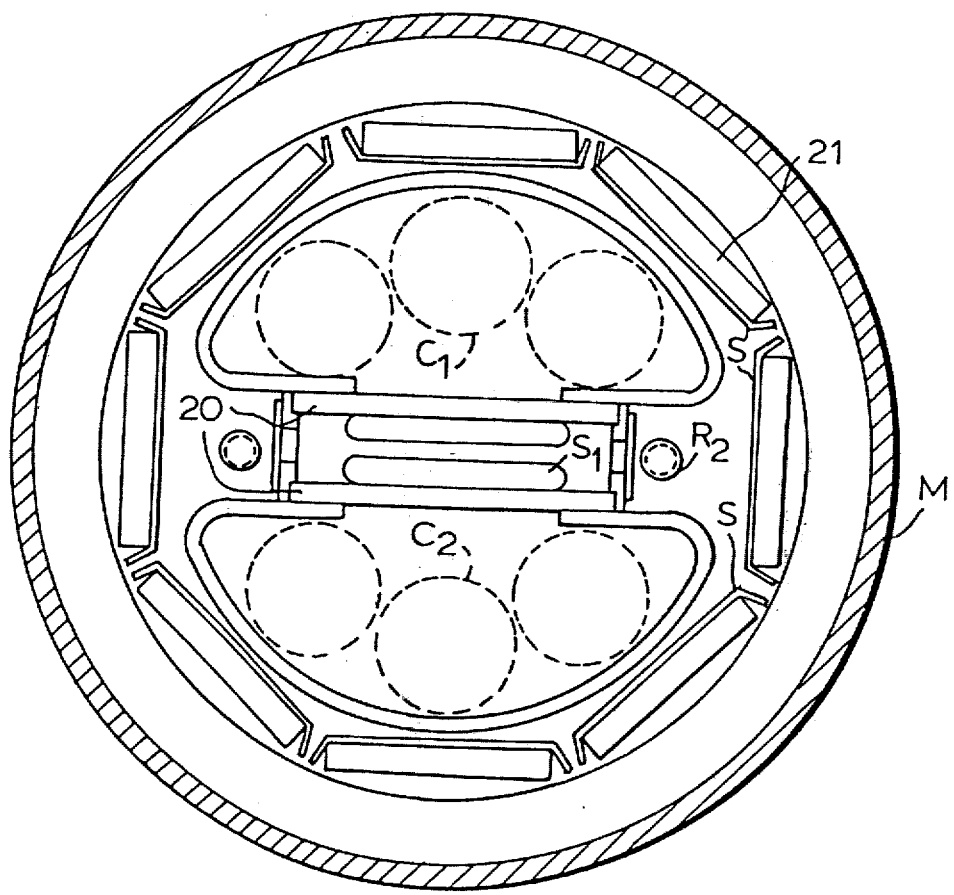
FIG. 6 is a transverse section taken along the line 6—6 of FIG 5, looking in the direction of the arrows.

A preferred construction is shown in FIG. 5 and in the transverse section thereof in FIG. 6, where the capacitors $C_1$, $C_2$, etc. of the bank are shown supported by vertical columns 20 on alternately opposite or staggered sides thereof (to reduce interstage coupling), with the spark gaps $S_1$, $S_2$, $S_3$, etc. in a vertical column therebetween, flanked by columns of the charging resistors $R_2$, etc. The triggering pin 46 is shown associated with the second gap $S_2$, as before explained. Further, the assembly is surrounded by a downwardly and outwardly tapered conical conductor or shield S (actually in octagonal sections, FIG. 6) which has been found to be as close a shielding arrangement as can be provided without breakdown problems and which materially reduces the volume occupied by the magnetic field set up during pulse generation, thus reducing the inductance significantly and desirably increasing capacitance to ground. This configuration has been found to aid in increasing the triggering range, as before discussed.

In practical apparatus of this type, highly successful production-line sterilization has been obtained with 75 nanoseconds pulses (full width at half maximum amplitude), produced at a repetition rate of 20 pulses/second at 225 Kv peak voltage and 2 kiloamps peak current. The electron beam width at windows 1 and 1' was about 4.0 cm. Synchronization of the line speed of the web W with the pulse repetition and dose-depth adjustments was effected such that for a 5 megarad surface dose, the line speed of the web W was adjusted to about 10 feet/minute, and the windows 1 and 1' of the gun cylinder generators 2 and 2' were tilted at about a 15° offset from facing one another. Under these conditions, a linear dose-depth profile close to that illustrated at "OPTIMUM" in FIG. 1 was obtained, and with at least about a 10-pulse overlap provided which, though the reliability of the system was very high, avoided even the remote statistical possibility of a spark-gap pre-breakdown or pulse miss, resulting in non-sterility. As an example, B-pumilis, a radiation-resistant spore, was effectively destroyed ($D_{10}$-value of 250 kilorads; i.e. 20 log treatment). Voltage-pulse ranges of $200\pm50$ Kv, with pulse widths (measured as before indicated) of the order of $80\pm20$ nanoseconds, and with pulse repitition frequencies of the order of $20\pm10$ pulses per second have been found most useful for certain sterilization purposes of the invention. Units involving products fed at higher line speeds (web speeds of about 25 meters per minute) are operable at repetition frequencies of the order of 100 pulses per second. As before stated, low energy electrons of the order of 50 to 450 keV are useful for the purposes of the invention, being generated by electric-discharge pulses of the order of 100 to 500 kV; and with pulse widths at one-half maximum of the order of 50 to 150 nanoseconds, and repetition frequencies of the order of 20 to 100 pulses per second.

While the invention has been described in connection with its important application to cold-cathode beam sterilization, features of the same may be used in other applications where similar advantages are desired, and the novel aspects of circuit and constructional details may also be used elsewhere as desired; further modifications occuring to those skilled in the art being deemed to fall within the spirit and scope of the invention as defined in the appended claims.

What is claimed is:

1. A process of insuring the reliability of the production of repetitive impulses of electron-beam energy for production-line irradiation purposes, that comprises, repetitively generating electric-discharge pulses; applying the pulses repetitively to draw electron beam impulses from a cold cathode to and through an electron-pervious window anode; disposing the window anode adjacent a portion of a region along which products-to-be-electron-beam irradiated are passed; causing the impedance presented by the cold cathode-window anode to the impedance presented by the pulse generating step to produce a substantially linear electron-beam dose versus penetration depth characteristic curve of relatively low slope compared to the DC characteristic curve in the region near the one-half dose region of said characteristic curves, thereby to reduce the sensitivity of the electron beam impulses to possible voltage variations during the pulse generating step in order to insure substantially uniform irradiation of the products passing along said region.

2. A process as claimed in claim 1 and in which the electron beam impulses are drawn as a periodic linear beam from a longitudinally extending cold cathode.

3. A process as claimed in claim 2 and in which said electric-discharge pulses are applied substantially simultaneously to draw a second set of electron beam impulses from a second cold cathode to and through a second electron-pervious window anode disposed adjacent the first-named window anode but directed toward a different portion of said region adjacent the first-named portion in order to prevent interference between the beams exiting the first-named and second window anodes.

4. A process as claimed in claim 3 and in which the portions of the said region respectively electron-beam-irradiated through the first-named and second window anodes are partially overlapping.

5. A process as claimed in claim 4 and in which the said repetition frequency is adjusted relative to the speed of passing of the products-to-be-irradiated through said region to provide a sufficient number of overlapping electron-beam impulses to obviate the effect of statistical misses in successive electric-discharge pulse generation.

6. A process as claimed in claim 5 and in which at least about ten overlapping electron-beam impulses are provided.

7. A process as claimed in claim 1 and in which said generating of electric-discharge pulses is effected by a Marx-type multiple gap-discharge array, triggering of said array being effected at the second gap of the array.

8. A process as claimed in claim 7 and in which shielding is effected along the gap-discharge array with successively increasing conducting surface surrounding the array.

9. A process as claimed in claim 1 and in which the generated electric-discharge pulses are of the order of 100 to 500 kV, with pulse widths at one-half maximum of the order of 50 to 150 nanoseconds, and repetition frequency of the order of 20 to 100 pulses per second.

10. Apparatus for electron-beam-irradiating surfaces passed along a predetermined region, having, in combination, electric-discharge repetitive pulse-generating means; electron gun means comprising cold cathode means and electron-pervious window anode means connected to the pulse-generating means repetitively to draw electron beam impulses from the cold cathode means to and through the window anode means; and means for disposing the window anode means adjacent a portion of said region along which products-to-be-electron-beam irradiated are passed; the relative impedances of the pulse-generating means and the electron gun means being predetermined to produce a substantially linear electron-beam dose versus penetration depth characteristic curve of relatively low slope compared to the DC characteristic curve in the region near the one-half dose region of said curves.

11. Apparatus as claimed in claim 10 and in which means is provided for adjusting the pulse repetition frequency of the pulse-generating means relative to the said product to cause treatment of the surfaces of the product most remote from said window anode to be near the one-half dose region of said characteristic curve.

12. Apparatus as claimed in claim 11 and in which a second similar electron gun means is provided also connected with said pulse-generating means substantially simultaneously to exit a second set of electron beam impulses through the window anode means thereof; means for disposing the window anode means of the second electron gun means adjacent the first-named window anode means but directed toward a different portion of said region adjacent the first-named portion in order to prevent interference between the beams exiting the first-named and second window anode means.

13. Apparatus as claimed in claim 12 and in which the portions of said region repetitively electron-beam-irradiated through the first-named and second window anode means are partially overlapping.

14. Apparatus as claimed in claim 10 and in which repetition frequency adjusting means is set to produce a repetition frequency relative to the speed of passing of the products-to-be-irradiated through said region to provide a sufficient number of overlapping electron beam impulses to guard against the effect of statistical misses in successive electric-discharge pulse generation.

15. Apparatus as claimed in claim 14 and in which said repetition frequency is set for at least about ten overlapping electron-beam impulses.

16. Apparatus as claimed in claim 10 and in which said electric discharge repetitive pulse-generating means comprises Marx-type generation means having a stacked array of discharge gaps connected with a corresponding staggered co-extensive array of capacitors, the final discharge of which is applied between the cold cathode means and window anode means of said electron gun means.

17. Apparatus as claimed in claim 16 and in which there is provided a charging circuit operative from line current and connected with capacitors, comprising rectifying means connected to the line current, high-frequency inverter means connected to the rectifying means for producing a high A.C. voltage output, and voltage doubler circuit means connected to receive said output.

18. Apparatus as claimed in claim 17 and in which said voltage doubler circuit means comprises pump capacitor means and bank capacitor means, the former being of small capacitance value relative to the capacitance of the bank capacitor means, and the latter serving as a capacitor of the said array of capacitors.

19. Apparatus as claimed in claim 16 and in which said pulse-generating means further comprises means for producing repetitive triggering pulses, and wherein there is provided trigger electrode means associated with the second of the discharge gaps and connected with the triggering pulse producing means.

20. Apparatus as claimed in claim 16 and in which there is provided conducting shield means surrounding said array of discharge gaps and capacitors and of successively increasing taper along said array.

21. Apparatus as claimed in claim 16 and in which the discharge gaps and corresponding capacitor arrays are disposed within a pressurized housing, and said electron gun means are evacuated.

22. Apparatus as claimed in claim 16 and in which said cold cathode means comprises substantially linear cathode strip means.

23. Apparatus as claimed in claim 16 and in which the said array of discharge gaps comprises a stack of substantially parallel pairs of spaced longitudinal rails.

24. Apparatus as claimed in claim 21 and in which high-voltage insulated bushing means is provided as a seal between the pressurized housing and the evacuated electron gun means, the bushing means also supporting the electrical connections between the pulse-generating means and the cold cathode means of said electron gun means.

* * * * *